US009987300B2

(12) United States Patent
Baert et al.

(10) Patent No.: US 9,987,300 B2
(45) Date of Patent: Jun. 5, 2018

(54) POLYINOSINIC-POLYCYTIDYLIC ACID (POLY (I:C)) FORMULATIONS FOR THE TREATMENT OF UPPER RESPIRATORY TRACT INFECTIONS

(71) Applicants: Lieven Elvire Colett Baert, Bruges (BE); Bruce Albert Malcolm, Burnaby (CA); Roger Paulus Maria Sutmuller, Bonheiden (BE)

(72) Inventors: Lieven Elvire Colett Baert, Bruges (BE); Bruce Albert Malcolm, Burnaby (CA); Roger Paulus Maria Sutmuller, Bonheiden (BE)

(73) Assignee: Janssen Sciences Ireland UC, Cork (IE)

( * ) Notice: Subject to any disclaimer, the term of this patent is extended or adjusted under 35 U.S.C. 154(b) by 0 days. days.

(21) Appl. No.: 15/180,603

(22) Filed: Jun. 13, 2016

(65) Prior Publication Data

US 2016/0296551 A1   Oct. 13, 2016

Related U.S. Application Data

(62) Division of application No. 14/398,573, filed as application No. PCT/EP2013/059079 on May 2, 2013.

(30) Foreign Application Priority Data

May 3, 2012 (EP) .................................. 12166595

(51) Int. Cl.
| | | |
|---|---|---|
| A61K 31/713 | (2006.01) | |
| A61K 9/00 | (2006.01) | |
| A61K 9/14 | (2006.01) | |
| A61K 9/16 | (2006.01) | |
| C12N 15/117 | (2010.01) | |

(52) U.S. Cl.
CPC .......... *A61K 31/713* (2013.01); *A61K 9/0043* (2013.01); *A61K 9/146* (2013.01); *A61K 9/16* (2013.01); *A61K 9/1617* (2013.01); *A61K 9/1623* (2013.01); *A61K 9/1652* (2013.01); *C12N 15/117* (2013.01); *C12N 2310/17* (2013.01); *C12N 2320/32* (2013.01)

(58) Field of Classification Search
CPC .. A61K 9/0043; A61K 9/1617; A61K 9/1623; A61K 9/1652; A61K 9/146; C12N 2310/17; C12N 2320/32
See application file for complete search history.

(56) References Cited

U.S. PATENT DOCUMENTS

| | | | | |
|---|---|---|---|---|
| 5,622,657 A | * | 4/1997 | Takada | A61K 9/1647 264/4.32 |
| 5,804,212 A | | 9/1998 | Ilium | |
| 6,468,558 B2 | * | 10/2002 | Wong | A61K 9/127 424/450 |
| 2001/0007665 A1 | | 7/2001 | Illum et al. | |
| 2002/0098203 A1 | * | 7/2002 | Gustavsson | A61K 9/1623 424/234.1 |
| 2004/0248837 A1 | | 12/2004 | Raz et al. | |
| 2005/0244505 A1 | * | 11/2005 | Higbee | A61K 9/1647 424/489 |
| 2006/0233715 A1 | | 10/2006 | Oki et al. | |
| 2007/0166239 A1 | | 7/2007 | Lin et al. | |
| 2010/0068206 A1 | | 3/2010 | Zeldis | |
| 2011/0244043 A1 | * | 10/2011 | Xu | A61K 9/0024 424/484 |
| 2012/0021006 A1 | * | 1/2012 | Levitzki | C12N 15/117 424/277.1 |
| 2012/0196875 A1 | | 8/2012 | Bouyssou et al. | |

FOREIGN PATENT DOCUMENTS

| | | | |
|---|---|---|---|
| CA | 1333258 C | 11/1994 | |
| CN | 101491503 A | 7/2009 | |
| CN | 101757018 A | 6/2010 | |
| JP | 2009209086 A | 9/2009 | |
| WO | WO-00/15262 A1 | 3/2000 | |
| WO | WO-2005072088 A2 | 8/2005 | |
| WO | WO 2009027337 A1 * | 3/2009 | ........... A61K 9/0043 |
| WO | WO-2009/136282 A1 | 11/2009 | |
| WO | WO 2010114169 A1 * | 10/2010 | ........... A61K 39/145 |
| WO | WO-2013164380 A1 | 11/2013 | |
| WO | WO-2015/067632 A1 | 5/2015 | |

OTHER PUBLICATIONS

Glanville et al (2015). "Challenges in developing a cross-serotype rhinovirus vaccine." Current Opinion in Virology, 11: 83-88.*
Simancas-Racines et al (2013). "Vaccines for the common cold (Review)." Cochrane Database of Systemic Reviews, 6: 1-33.*
Jacobs et al (2013). "Human Rhinoviruses". Clin Microbiol Rev, 26(1): 135-162.*
A phase I double-blind, placebo-controlled, dose-escalating study to evaluate the safety and tolerability of topical nasal poly-ICLC. NIAID; Clinical Trial Protocol NCT00646152, 2008.
Avila, P.C. et.al. (2000). Effects of allergic inflammation of the nasal mucosa on the severity of rhinovirus 16 cold, J Allergy Clin Immunol, 105 (5) 923-32. doi: 10.1067/mai.2000.106214.
Boukhvalova, M.S. et.al. (2010). Activation of interferon response through toll-like receptor 3 impacts viral pathogenesis and pulmonary toll-like receptor expression during respiratory syncytial virus and influenza infections in the cotton rat *Sigmodon hispidus* model. J Interferon Cytokine Res, 30 (4) 229-42. doi: 10.1089/jir.2009.0025.

(Continued)

*Primary Examiner* — Anoop K Singh
*Assistant Examiner* — Doan T Phan
(74) *Attorney, Agent, or Firm* — David Halstead; Foley Hoag LLP

(57) ABSTRACT

The present invention concerns a composition comprising micro particles of polyinosinic-polycytidylic acid (Poly (I:C)) and a carrier polymer selected from starch, alginate, blanose or DPPC (dipalmitoylphosphatidylcholine) for use in preventing and/or treating viral infections of the upper respiratory tract or the common cold and a device, preferably a nasal delivery system, comprising said composition for use by a patient in need to prevent and/or treat infections or the common cold.

17 Claims, 16 Drawing Sheets

(56) References Cited

OTHER PUBLICATIONS

Chayama, K. and Hayes, C.N. (2015). HCV Drug Resistance Challenges in Japan: The Role of Pre-Existing Variants and Emerging Resistant Strains in Direct Acting Antiviral Therapy. Viruses, 7 (10) 5328-42. doi: 10.3390/v7102876.
Christopher et al., "Use of toll-like receptor 3 agonists against respiratory viral infections," Anti-Inflammatory & Anti-Allergy Agents in Med Chem, 10(5):327-38 (2011).
Christopher, M. E., & Wong, J. P. (2008). Broad-spectrum drugs against viral agents. Int J Mol Sci, 9(9), 1561-1594. doi:10.3390/ijms9091561.
De Clercq, E. (1979). Degradation of poly(inosinic acid)-poly(cytidylic acid) [(I)n—(C)n] by human plasma. Eur J Biochem. 93 (1), 165-72.
De Clercq, E., Krajewska, E., Descamps, J., & Torrence, P. F. (1977). Anti-herpes activity of deoxythymidine analogues: specific dependence on virus-induced deoxythymidine kinase. Mol Pharmacol, 13(5), 980-984.
DeVincenzo, J, t. al. (2010). A randomized, double-blind, placebo-controlled study of an RNAi-based therapy directed against respiratory syncytial virus. Proc Natl Acad Sci 107 (19), 8800-5. doi: 10.1073/pnas.0912186107.
DeVincenzo, J., Cehelsky, J. E., Alvarez, R., Elbashir, S., Harborth, J., Toudjarska, I., Meyers, R. (2008). Evaluation of the safety, tolerability and pharmacokinetics of ALN RSV01, a novel RNAi antiviral therapeutic directed against respiratory syncytial virus (RSV). Antiviral Res, 77(3), 225-231. doi:10.1016/j.antiviral.2007.11.009.
Fenje, P. and Postic, B. (1971). Prophylaxis of experimental rabies with the polyriboinosinic-polyribocytidylic acid complex. J Infect Dis, 123 (4) 426-8.
Field AK, Tytell AA, Piperno E, Lampson GP, Nemes MM, Hilleman MR. Poly I:C, an inducer of interferon and interference against virus infections. Medicine 1972; 51(3): 169-174.
Field, A. K., Lampson, G. P., Tytell, A. A., Nemes, M. M., & Hilleman, M. R. (1967). Inducers of interferon and host resistance, IV. Double-stranded replicative form RNA (M52-Ff-RNA) from E. coli infected with MS2 coliphage. Proc Natl Acad Sci U S A, 58(5), 2102-2108.
Field, A. K., Tytell, A. A., Lampson, G. P., & Hilleman, M. R. (1967). Inducers of interferon and host resistance. II. Multistranded synthetic polynucleotide complexes. Proc Natl Acad Sci U S A, 58(3), 1004-1010.
Hafner, A.M., et.al. Particulate formulations for the delivery of poly(I:C) as vaccine adjuvant. Adv Drug Deliv Rev, 65 (10), 1386-99. doi: 10.1016/j.addr.2013.05.013.
Heffernan et al., The stimulation of CD8+ T cells by dendritic cells pulsed with polyketal microparticles containing ion-paired protein antigen and poly(inosinic acid)-poly(cytidylic acid), Biomaterials, 30(5):910-8 (2009).
Hill, D.A. et.al (1972). Evaluation of an interferon inducer in viral respiratory disease. JAMA, 219 (9) 1179-84.
Homan, E.R. et.al. (1972). Studies on poly I:C toxicity in experimental animals. Toxicol Appl Pharmacol. 23 (4), 579-88.
Ichinohe, T., et. al. (2005). Synthetic double-stranded RNA poly(I:C) combined with mucosal vaccine protects against influenza virus infection. J. Virol. 79 (5) 2910-9. doi: 10.1128/JVI.79.5.2910-2919.2005.
Kawai, T & Akira, S. (2010). The role of pattern-recognition receptors in innate immunity: update on Toll-like receptors. Nat Immunol. 11 (5), 373-84.
Lienenklaus, S., Cornitescu, M., Zietara, N., Lyszkiewicz, M., Gekara, N., Jablonska, J, Weiss, S. (2009). Novel reporter mouse reveals constitutive and inflammatory expression of IFN-beta in vivo. J Immunol, 183(5), 3229-3236. doi:10.4049/jimmunol. 0804277.
Martins, K.A. et al. Vaccine adjuvant uses of poly-IC and derivatives. Expert Rev Vaccines, 14 (3), 447-59. doi: 10.1586/14760584. 2015.966085.

Mazaleuskaya, L. et. al. (2012). Protective role of Toll-like Receptor 3-induced type I interferon in murine coronavirus infection of macrophages. Viruses, 4 (5) 901-23. doi: 10.3390/v4050901.
Mendlowski, B. et.al. (1975). Safety assessment of poly I:C in NZB/NZW mice (38565). Proc Soc Exp Biol Med. 148 (2), 476-83.
Nemes, M.M., et. al. (1969). Inducers of interferon and host resistance. VI. Antiviral efficacy of poly I:C in animal models. Proc Soc Exp Biol Med, 132 (2) 776-83.
Nordlund, J.J. et.al. (1970). Inhibition of biologic activity of poly I: poly C by human plasma. Proc Soc Exp Biol Med. 133 (2), 439-44.
Okabayashi, T. (2011). Type-III interferon, not type-I, is the predominant interferon induced by respiratory viruses in nasal epithelial cells. Virus Res, 160 (1-2), 360-6). doi: 10.1016/j.virusres.2011. 07.011.
Overton, E. T. et. al. Intranasal seasonal influenza vaccine and a TLR-3 agonist, rintatolimod, induced cross-reactive IgA antibody formation against avian H5NI and H7N9 influenza HA in humans. Vaccine, 32 (42), 5490-5. doi: 10.1016/j.vaccine.2014.07.078.
Ozsoy et al., 2009. Nasal Delivery of High Molecular Weight Drugs. Molecules, 2009, 14, 3754-3779.
Park J.H. and Baron, S. (1968). Herpetic keratoconjunctivitis: therapy with synthetic double-stranded RNA. Science, 162 (3855) 811-3.
Pereswetoff-Morath, L. (1998). Microspheres as nasal drug delivery systems. Adv. Drug Del Rev, 29 (1-2), 185-194.
Phillips, B.M. et.al. (1971). Systemic toxicity of polyinosinic acid: polycytidylic acid in rodents and dogs. Toxicol Appl Pharmacol. 18 (1), 220-30.
Pérez, S & Bertoft, E. (2010). The molecular structures of starch components and their contribution to the architecture of starch granules: A comprehensive review. Starch, 62 (8), 389-420. doi: 10.1002/star.201000013.
Sadler, A.J & Williams, B.R. (2008). Interferon-inducible antiviral effectors. Nat Rev Immunol. 8 (7). 559-68. doi: 10.1038/nri2314.
Stetson, D.B. and Medzhitov, R. (2006). Recognition of cytosolic DNA activates an IRF3-dependent innate immune response. Immunity, 24 (1), 93-103). doi: 10.1016/j.immuni.2005.12.003.
Stowell, N. C. et. al. (2009). Long-term activation of TLR3 by poly(I:C) induces inflammation and impairs lung function in mice. Respir Res. 10. doi: 10.1186/1465-9921-10-43.
Triantafilou, M. et.al. (2011). Location, location, location: is membrane partitioning everything when it comes to innate immune activation? Mediators Inflamm.
Vivien, P. et al (1994) Nasal absorption of MCP formulations. Eur J. Pharm Biopharm 40(4), 228-31.
Wong et al., "Liposome-mediated immunotherapy against respiratory influenza virus infection using double-stranded RNA poly ICLC," Vaccine, 17(13-14):1788-95 (1999).
Wong JP, Nagata LP, Christopher ME, Salazar AM, Dale RM. Prophylaxis of acute respiratory virus infections using nucleic acid-based drugs. Vaccine. Mar. 18, 2005;23(1718):2266-8.
Yoneyama, M., et.al. (2004). The RNA helicase RIG-I has an essential function in double-stranded RNA-induced innate antiviral responses. Nat Immunol. 5 (7), 730-7.
Zhao, J. et.al. (2012)Intranasal treatment with poly(I*C) protects aged mice from lethal respiratory virus infections. J Virol, 86 (21) 11416-24. doi: 10.1128/JVI.01410-12.
Zhao, J. et.al. (2014). Rapid generation of a mouse model for Middle East respiratory syndrome. Proc Natl Acad Sci, 111 (13) 4970-5. doi: 10.1073/pnas.1323279111.
Guidance for Industry: Nasal Spray and Inhalation Solution, Suspension, and Spray Drug Products—Chemistry, Manufacturing, and Controls; Documentation. Jul. 31, 2002; p. 7 Section 2. Excipients paragraph 1.
International Search Report and Written Opinion for Singapore Patent Application No. 11201603570R dated Apr. 25, 2017.
Notice of Allowance and Fees Due for U.S. Appl. No. 14/398,573 dated Apr. 24, 2017.
Steffens, "Application of Starches, Modified Starches and Starch Derivatives in; Pharmaceutical Products," Apr. 28, 2006; pp. 2 and 17.

(56) References Cited

OTHER PUBLICATIONS

Bilancetti et al., "A Statistical Approach to Optimize the Spray Drying of Starch Particles: Application to Dry Powder Coating," AAPS PharmSciTech, 11(3): 1257-1267 (2010).
DeWitte-Orr et al., "Long Double-Stranded RNA Induces an Antiviral Response Independent of IFN Regulatory Factor 3, IFN-B Promoter Stimulator 1, and IFN." J Immunology., 183; 6545-6553 (2009).
Jewell et al., "In situ engineering of the lymph node microenvironment via intranodal injection of adjuvant-releasing polymer particles," Proc Nat Acad Sci U S A, 108(38)15745-15750 (2011).
Traves et al., "Viral-associated exacerbations of asthma and COPD," Curr Opin Pharm., 7:252-258 (2007).
Wischke et al., "Poly (I: C) coated PLGA microparticles induce dendritic cell maturation," Int J Pharmaceut, 365(1-2):61-68 (2009).

* cited by examiner

POLYINOSINIC-POLYCYTIDYLIC ACID (POLY (I:C)) FORMULATIONS FOR THE TREATMENT OF UPPER RESPIRATORY TRACT INFECTIONS

CROSS-REFERENCE TO RELATED APPLICATIONS

This application is a divisional of U.S. patent application Ser. No. 14/398,573, filed Nov. 3, 2014, which is a national stage application of PCT Application Number PCT/EP2013/059079, filed May 2, 2013, which claims priority to European Patent Application Number EP12166595.4, filed May 3, 2012. The entire content of each of the foregoing applications is incorporated herein by reference in its entirety.

BACKGROUND OF THE INVENTION

Field of the Invention

The present invention relates to a composition comprising micro particles of polyinosinic-polycytidylic acid (Poly (I:C)) and a carrier polymer selected from starch, alginate, blanose or DPPC (dipalmitoylphosphatidylcholine) for use in treating and/or preventing infections or the common cold and a device, preferably a nasal delivery system, comprising said composition for use by a patient in need to prevent and/or treat infections or the common cold.

Description of Related Art

The common cold (also known as nasopharyngitis, acute viral rhinopharyngitis, acute coryza, or a cold) is a viral infectious disease of the upper respiratory system caused primarily by viruses.

Viruses

The common cold is a viral infection of the upper respiratory tract. The most commonly implicated virus is the rhinovirus (30-50%), a type of picomavirus with 99 known serotypes. Others include coronavirus (10-15%), influenza (5-15%), human parainfluenza viruses, human respiratory syncytial virus, adenoviruses, enteroviruses, and metapneumovirus.

In total over 200 serologically different viral types cause colds. Coronaviruses are particularly implicated in adult colds. Of over 30 coronaviruses, 3 or 4 cause infections in humans, but they are difficult to grow in the laboratory and their significance is thus less well-understood. Due to the many different types of viruses and their tendency for continuous mutation, it is impossible to gain complete immunity to the common cold.

Clinical Signs and Symptoms

The first indication of an upper respiratory virus is often a sore or scratchy throat. Other common symptoms are runny nose, congestion, and sneezing. These are sometimes accompanied by conjunctivitis (pink eye), muscle aches, fatigue, malaise, headache, weakness, or loss of appetite. Cough and fever generally indicate influenza rather than an upper respiratory virus with a positive predictive value of around 80%. Symptoms may be more severe in infants and young children, and in these cases it may include fever and hives. Upper respiratory viruses may also be more severe in smokers.

Viral replication begins 2 to 6 hours after initial contact. Symptoms usually begin 2 to 5 days after initial infection but occasionally occur in as little as 10 hours. Symptoms peak 2-3 days after symptom onset, whereas influenza symptom onset is constant and immediate. There is currently no known treatment that shortens the duration; however, symptoms usually resolve spontaneously in 7 to 10 days, with some symptoms possibly lasting for up to three weeks. In children the cough lasts for more than 10 days in 35-40% and continues for more than 25 days in 10% of the cases. The common cold is the most frequent infectious disease in humans with the average adult contracting two to four infections a year and the average child contracting several infections per year between 6-12 years of age. In the United States, the incidence of colds is higher in the fall (autumn) and winter, with most infections occurring between September and April. The seasonality may be due to the start of the school year or due to people spending more time indoors (in closer proximity with each other) increasing the chance of transmission of the virus.

Infectious Period

The common cold is most infectious during the first two to three days of symptoms however it is also infectious for a couple of days before the onset of symptoms and may still be somewhat infectious until symptoms have completely resolved.

Human Rhinovirus

Human rhinovirus is a member of the Enterovirus genus in the Picomaviridae family. The HRV particle is comprised of a 27-30 nm non-enveloped capsid consisting of 4 polypeptides (VP1, VP2, VP3, and VP4). The virus capsid contains a single-stranded RNA genome of approximately 7200 bases. A virally-encoded protein (VPg) is covalently attached to the 5' end of the RNA genome. The clinical course of infection with human rhinovirus (HRV) has been well characterized. HRVs can infect the upper and lower airways, nasal mucosa, sinuses and middle ear, and infections produce symptoms of "the common cold" (see above). Infections are self-limiting and are typically restricted to the upper airways. Peripheral white blood cell counts may be elevated during the first 2-3 days of the infection.

HRV infection can also lead to infection of the lower airways, otitis media (particularly in young children), and sinusitis. Serious complications (such as pneumonia) from rhinovirus infection are rare and have been reported to occur in infants and young children, particularly those with underlying conditions such as bronchopulmonary dysplasia, congenital heart disease, prematurity, and neurologic conditions, and immunosuppressed (bone marrow transplant recipients) adults. While other members of the Picomaviridae family can infect the central nervous system (i.e., poliovirus, enterovirus), infection of the human central nervous system by HRVs has not been reported.

Treatment

There are no commercial antiviral agents for the treatment of rhinovirus infections or prevention of common colds. Treatment of upper respiratory tract infections caused by rhinoviruses are based upon management of the symptoms (sneezing, nasal congestion, rhinorrhea, eye irritation, sore throat, cough, headaches, fever, chills) typically using over the counter antihistamines, aspirin, cough suppressants, and nasal decongestants. More serious complications of HRVs infection (e.g. pneumonia) are managed using medically appropriate standards of care.

Cost and Medical Need

According to data of the World Health Organization more than 1 billion cases of common cold were reported in the USA last year. In the United States, the common cold leads to 75 to 100 million physician visits annually at a conservative cost estimate of $7.7 billion per year. Americans spend $2.9 billion on over-the-counter drugs and another $400 million on prescription medicines for symptomatic relief. An estimated 22 to 189 million school days are missed annually due to a cold. As a result, parents missed 126 million workdays to stay home to care for their children. When added to the 150 million workdays missed by employees suffering from a cold, the total economic impact of cold-related work loss exceeds $20 billion per year. This accounts for 40% of time lost from work.

BRIEF SUMMARY OF HOT INVENTION

One aspect of the invention is a composition comprising micro particles of polyinosinic-polycytidylic acid (Poly (I:C)) and a carrier polymer selected from starch, alginate, blanose or dipalmitoylphosphatidylcholine (DPPC).

Another aspect of the invention is a method of treating upper respiratory infections or common cold by administering to a patient in need thereof a therapeutically effective amount of the composition of claim 1 for a time period to treat infections or common cold.

Another aspect of the invention is a device for nasal delivery, comprising the composition of the invention.

DETAILED DESCRIPTION OF THE INVENTION

Figure 1A:
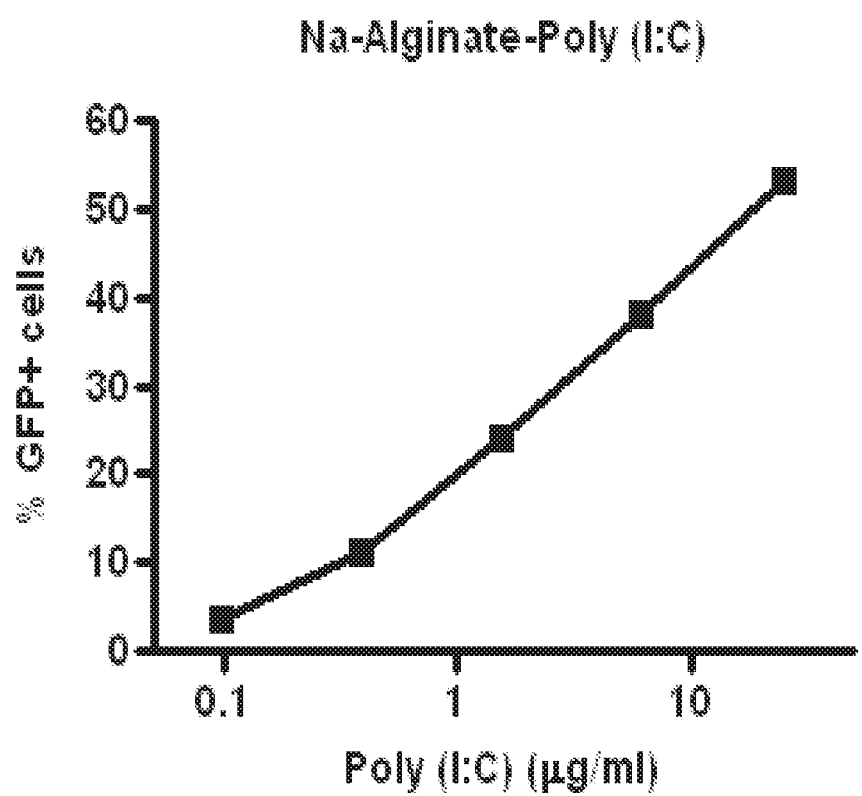
FIG. 1A shows biological (interferon) stimulating capacity of Poly (I:C)-Na-alginate carrier mixtures as assessed by GFP expression under the interferon-β-promoter. Numbers on the Y-axis indicate the percentage of GFP+ cells of the total living cells in the sample. Numbers on the x-axis indicate the concentration of Poly (I:C) in the mixture. Representative results of two experiments are shown.
Figure 1B:
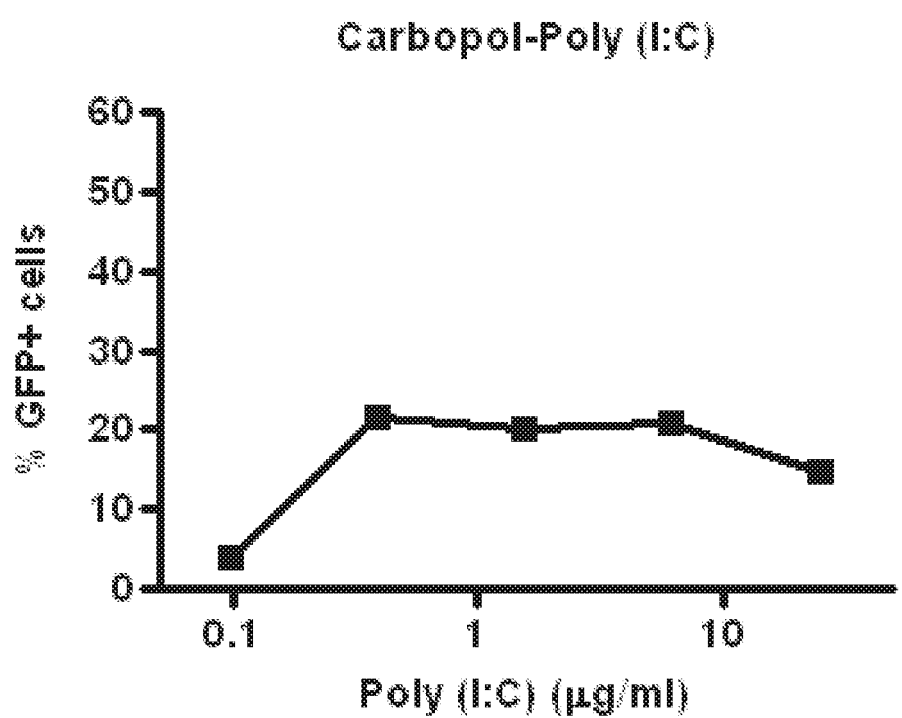
FIG. 1B shows the same experiment as described in FIG. 1A except that the carrier is carbopol.
Figure 1C:
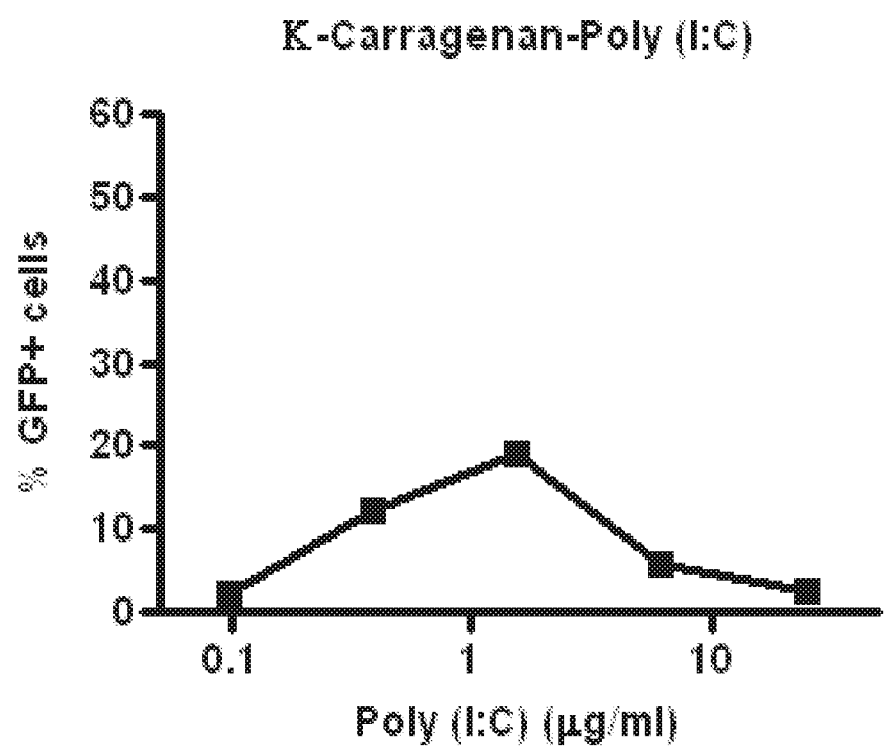
FIG. 1C shows the same experiment as described in FIG. 1A except that the carrier is K-carragenan.
Figure 1D:
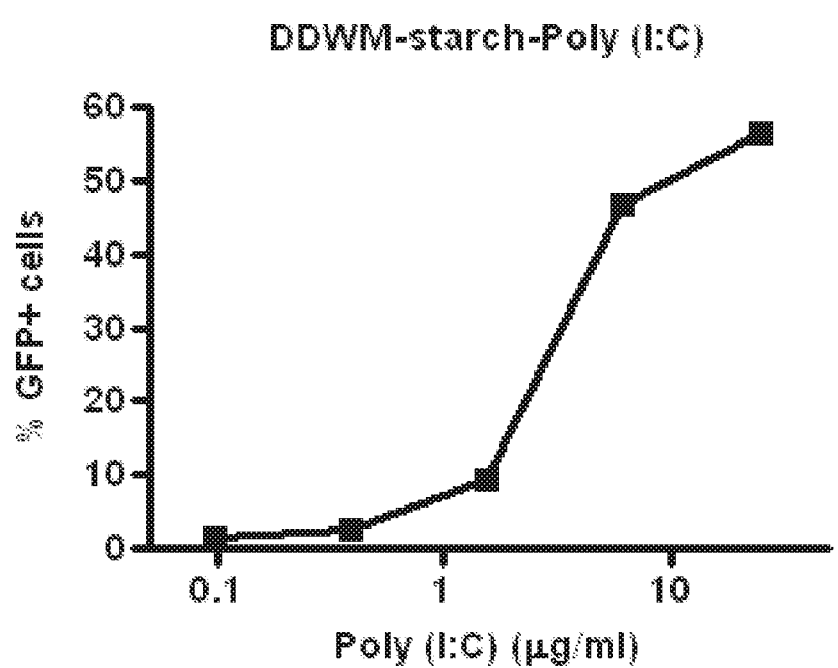
FIG. 1D shows the same experiment as described in FIG. 1A except that the carrier is DDWM-starch.
Figure 1E:
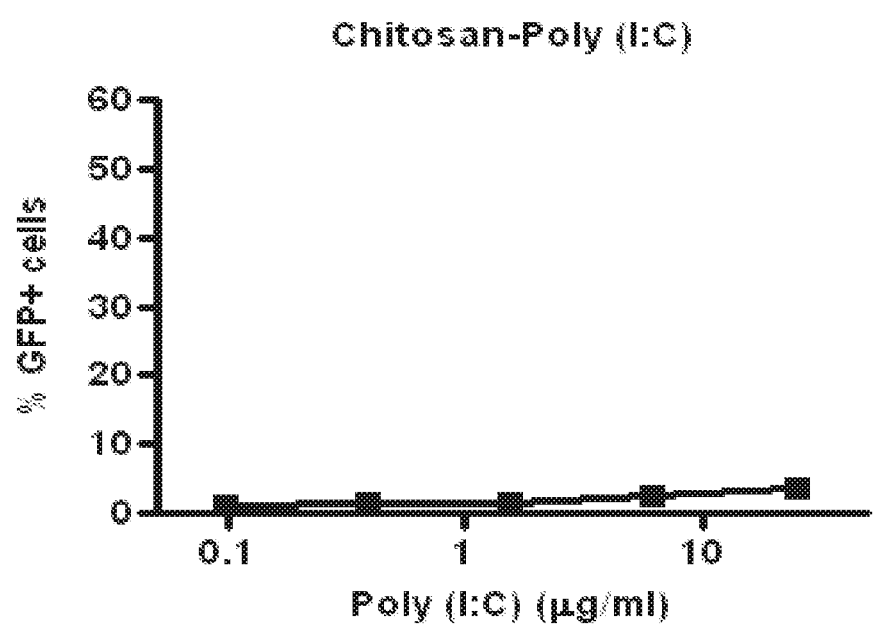
FIG. 1E shows the same experiment as described in FIG. 1A except that the carrier is chitosan.
Figure 1F:
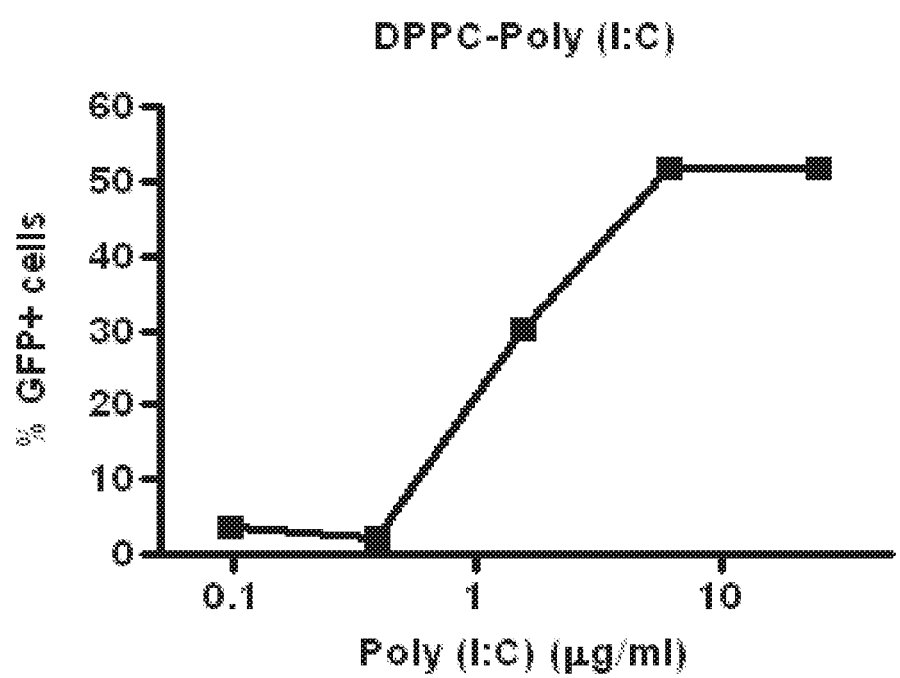
FIG. 1F shows the same experiment as described in FIG. 1A except that the carrier is DPPC.
Figure 1G:
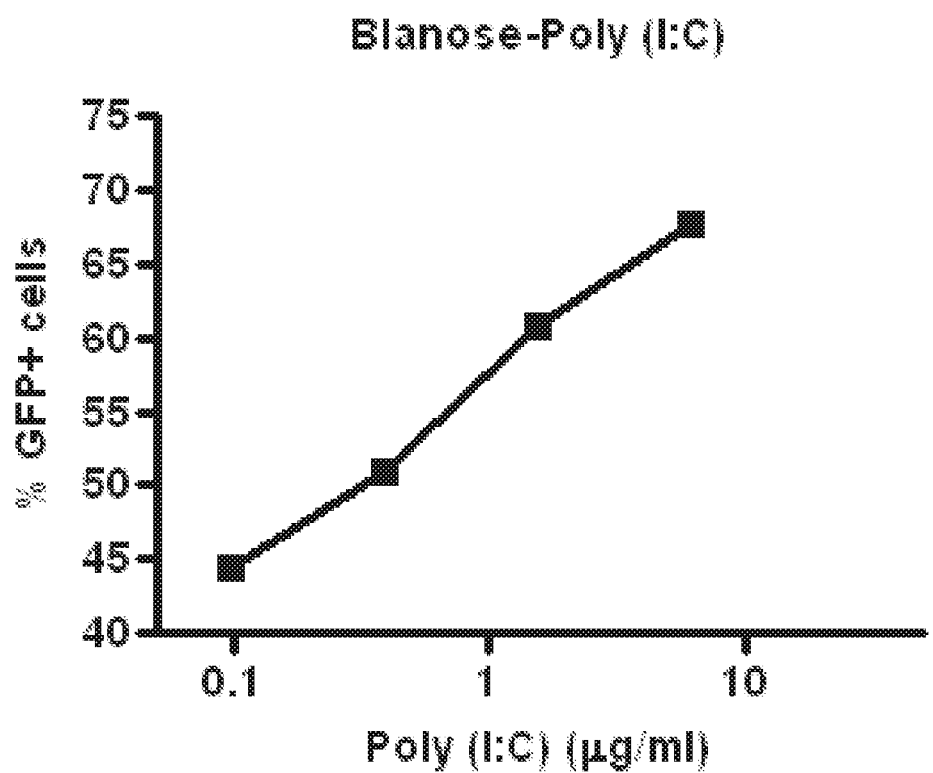
FIG. 1G shows the same experiment as described in FIG. 1A except that the carrier is blanose.
Figure 1H:
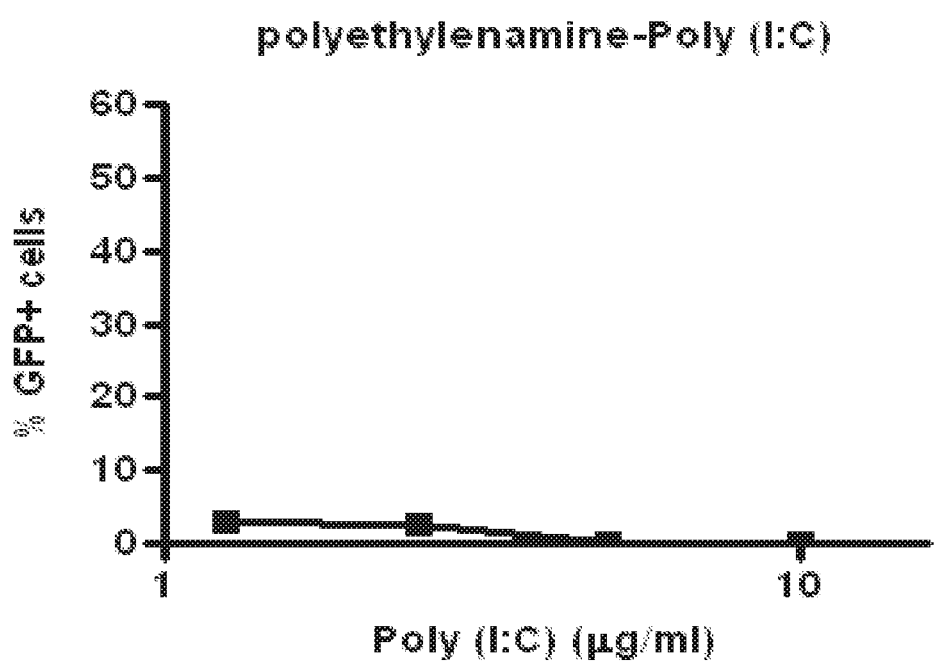
FIG. 1H shows the same experiment as described in FIG. 1A except that the carrier is polyethylenamine.
Figure 1I:
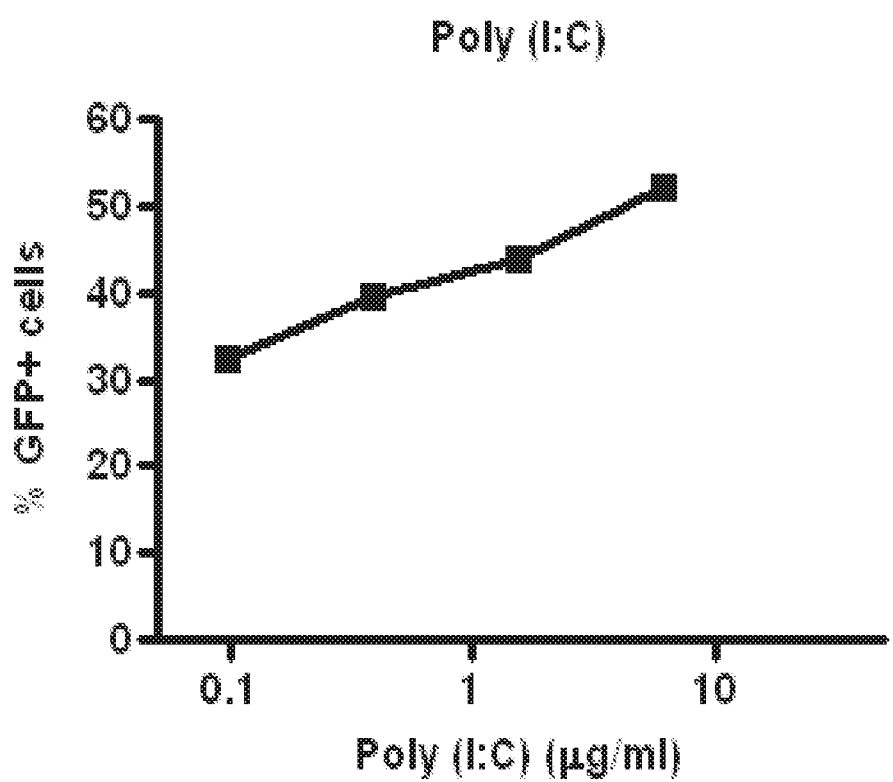
FIG. 1I shows biological (interferon) stimulating capacity of Poly (I:C) alone as assessed by GFP expression under the interferon-1-promoter. Numbers on the Y-axis indicate the percentage of GFP+ cells of the total living cells in the sample. Numbers on the x-axis indicate the concentration of Poly (I:C) in the mixture. Representative results of two experiments are shown.

Airway epithelial cells are the primary target of upper respiratory tract (URT) infective agents like rhino- and corona viruses. As infection with these viruses occurs prior to the onset of symptoms that reflects immune system clearance of infected cells, direct antiviral therapeutic intervention is unlikely to prove very effective. In addition, realizing and sustaining active levels of direct anti-viral compounds in the nasal mucosa is very difficult due to its high turnover. Prophylaxis on the other hand, by exploiting the body's own defenses and inducing an anti-viral state in the nasal epithelial cells, has already been shown to result in significant protection against a subsequent viral challenge as well as to lower the disease-related symptoms.

Although colds may last only a week or two, severe colds can last for up to a month. Adults average two to three colds per year and children six to ten, depending on their age and exposure. There are hundreds of different serotypes of the cold virus, making it impossible to develop a standard vaccine prophylaxis that would be effective against all of them.

Symptomatic treatment generally involves using sleep-inducing oral anti-histamines and/or vaso-constrictive decongestants that have stimulant side-effects. This is only marginally effective and these side-effects are often as debilitating as the infection itself. Although prevention would be the ideal solution, for the reasons cited above the chances of a broadly effective vaccine against all the different serotypes is highly unlikely in the near future. So, short of quarantine, people will be exposed to these infectious agents on a regular basis, especially during "cold season" and so a broadly effective, convenient, side-effect free prophylactic would have a major impact on public health and productivity in the work place.

Targeting the innante immune response, an "early warning system" for the body would solve the above mentioned issues. This system, present in nasal epithelial cells, once stimulated appropriately, leads the cells to think they are being attacked by a virus and triggers an anti-viral defense response. Once this happens, the cells are refractory to subsequent viral attack. Although some early work had been done in the late 1980's, looking at the use of immune stimulating molecules such as interferon to trigger an innate immune response, manufacture was expensive and their effects difficult to control.

The goal of the current investigation has been to develop a formulation of a triggering molecule (Poly (I:C)) that can be used in a measurable and controllable fashion, for example, every couple of days or even once a week, to prime the innate immune system and provide protection against viral infection. The approach outlined below takes an existing agent, Poly (I:C), which has demonstrated efficacy, but which is impractical and renders it convenient and effective using formulation sciences.

Toll-like receptor 3 (TLR3) is a protein that in humans is encoded by the TLR3 gene. TLR3 is a member of the Toll-like receptor family of pattern recognition receptors of the innate immune system which plays a fundamental role in pathogen recognition and activation of innate immunity. TLRs are highly conserved from *Drosophila* to humans and share structural and functional similarities. They recognize pathogen-associated molecular patterns (PAMPs) that are expressed on infectious agents, and mediate the production of cytokines necessary for the development of effective immunity. The various TLRs exhibit different patterns of expression. This TLR3 receptor is also expressed by airway epithelial cells and is restricted to the dendritic subpopulation of the leukocytes.

TLR3 recognizes double-stranded RNA (dsRNA). Double-stranded RNA is RNA with two complementary strands that can be formed during the viral replication cycle. Upon recognition, TLR 3 induces the activation of transcription factors like NF-κB and Interferon Regulatory Factor 3 (IRF3) to increase production of type I interferons which signal other cells to increase their antiviral defenses.

The structure of TLR3 forms a large horseshoe shape that contacts with a neighboring horseshoe, forming a "dimer" of two horseshoes. Much of the TLR3 protein surface is covered with sugar molecules, making it a glycoprotein, but on one face (including the proposed interface between the two horseshoes), there is a large sugar-free surface. This surface also contains two distinct patches rich in positively-charged amino acids, which may be a binding site for negatively-charged double-stranded RNA.

Polyinosine-polycytidylic acid (Poly (I:C)) is a double stranded RNA molecule with a MW distribution up to 1,000,000 Daltons. Poly (I:C) is a Toll Like Receptor 3 (TLR3) ligand that mimics viral RNA and is a known stimulant of the innate immune response. When administered nasally it induces expression of anti-viral proteins like Interferon α and β in the nasal epithelium. It has been demonstrated to reduce the number and severity of rhinovirus infections.

Poly (I:C) is an unstable molecule in aqueous solutions. Currently, to achieve an effective therapeutic or prophylactic effect, Poly (I:C) needs to be re-dissolved immediately prior to use and administered every 2 hours. To improve patient compliance and reduce the frequency of dosing, a novel formulation has been developed that is stable and shows enhanced efficacy Poly (I:C) has been formulated with several bioadhesive polymers that can prolong the residence time on the nasal epithelium and provide a more effective and controllable stimulation of the innate immune system.

The current invention provides the identification of a unique formulation that could be stored almost indefinitely at room temperature and which retains its innate immune system-stimulating activity.

In addition the formulation enhances the efficacy of Poly (I:C) and permits much less frequent dosing with even greater TLR3 stimulating activity.

The invention therefore relates to a composition comprising micro particles of polyinosinic-polycytidylic acid (Poly (I:C)) and a carrier polymer selected from starch, alginate, blanose or DPPC (dipalmitoylphosphatidylcholine). Micro particles are particles with an average particle size between 0.1 μm and 100 μm. Preferably the carrier polymer is starch obtained from maize, potato or cassava.

Poly (I:C)-carrier-polymer microspheres, or also so-called micro particles, comprised in the composition are produced by means of a particle formation process such as a spray-dry process.

The ratio Poly (I:C)/starch according to the invention ranges from 1/200 (w/w) to 1/0.1 (w/w), but preferably from 1/100 (w/w) to 1/1 (w/w) and even more preferably from 1/100 (w/w) to 1/5 (w/w) while a ratio Poly (I:C)/starch between 1/12 and 1/9 (w/w) is most preferred.

The $D_v50$ (=volume based 50% cumulative undersize of the particle) of the micro particle in the composition according to the invention ranges from 0.1 micrometer to 200 micrometer, preferably from 1 micrometer to 50 micrometer, more preferably from 2 micrometer to 40 micrometer, even more preferably from 2 micrometer to 20 micrometer, and most preferred from 10 micrometer to 20 micrometer.

The composition of the invention can also be a liquid composition comprising an organic solvent, wherein the organic solvent is based on glycerol or ethanol or a combination thereof.

The composition of the invention can be used in medicine preferably for use in preventing and/or treating viral infections of the upper respiratory tract such as what are referred to as "common colds".

The current composition can be used by patients suffering from asthma and/or COPD (Chronic Obstructive Pulmonary Disease) in order to potentially prevent and/or treat upcoming common cold symptoms.

A preferred way to prevent and/or treat upper respiratory infections is performed by nasal administration.

The composition of the current invention comprising micro particles of polyinosinic-polycytidylic acid (Poly (I:C)) and a carrier polymer selected from starch, alginate, blanose or DPPC (dipalmitoylphosphatidylcholine) can be used for the treatment and/or prevention of (viral) infections or common cold, wherein the composition is administered by nasal application at a time interval that is in the range of one day to one month, more preferably from every couple of days or even once a week.

The above mentioned composition wherein the ratio Poly (I:C)/starch ranges from 1/200 (w/w) to 1/0.1 (w/w), but preferably from 1/100 (w/w) to 1/1 (w/w) and even more preferably from 1/100 (w/w) to 1/5 (w/w) while a ratio Poly (I:C)/starch between 1/12 and 1/9 (w/w) is most preferred, in combination with the micro particle size in the composition ranging from 0.1 micrometer to 200 micrometer, preferably from 1 micrometer to 50 micrometer, more preferably from 2 micrometer to 40 micrometer, even more preferably from 2 micrometer to 20 micrometer, and most preferred from 10 micrometer to 20 micrometer can be used for the treatment and/or prevention of (viral) infections or common cold, wherein said composition is administered by nasal application at a time interval that is in the range of one day to one month, more preferably from every couple of days or even once a week.

Part of the invention is also a device, in particular a nasal delivery system, comprising a composition according to the invention.

According to the invention, Poly (I:C) is formulated as a dry powder for nasal administration. To improve stability, Poly (I:C) is spray dried from an aqueous mixture containing drum dried waxy maize starch and Poly (I:C).

Starch is believed to have a dual function: (1) to act as a bio-adhesive in the nose, (2) the amylopectin present in high concentration in waxy maize starch is broken down by amylases in the nose to release Poly (I:C).

Nasal administration is preferably achieved using a single dose nasal powder device (Unit dose device supplied from Aptar Pharma Germany). The unit dose device is an active delivery system, meaning that the patient does not need to inhale and performance is patient independent. Dosing is performed by actuation, which is controlled by overpressure. The dose per puff is determined by the concentration of Poly (I:C) in the spray dried powder and the emitted weight of the powder. The powder will be administered into each nostril using a new device for each puff.

As mentioned above Poly (I:C), is a synthetic double-stranded RNA composed of anti-parallel polynucleotide strands of inosinic acid and cytidylic acid sodium salts. The strands are non-covalently bound by hydrogen bonds formed between the inosine and cytosine bases.

The average chain length for the Poly (I:C) ranges between 300 to 6,000 base pairs, corresponding to approximately 180,000 to 3,600,000 daltons. The molecular formula is $(C_{10}H_{10}N_4NaO_7P)_x.(C_9H_{11}NaN_3OP)_x$.

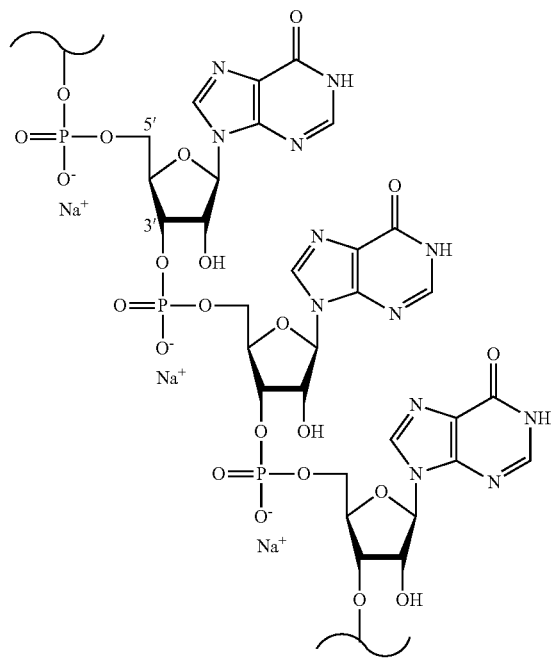

Polyinosinic Acid

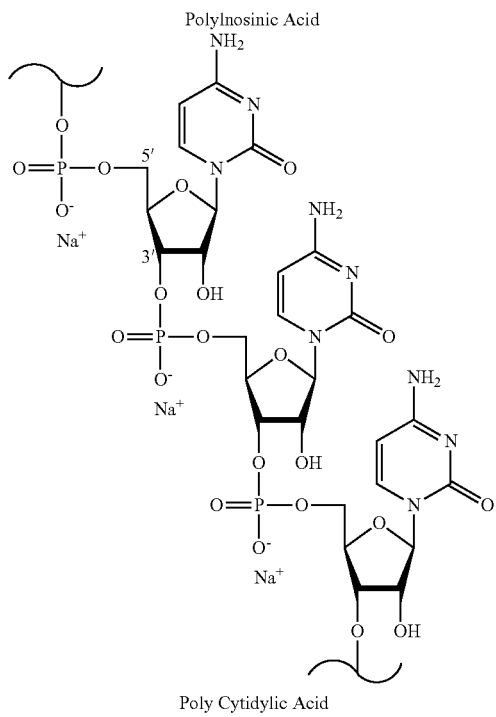

Poly Cytidylic Acid

Above Poly (I:C) can be purchased, but can optionally also be made in house using for instance the following procedure The duplex product Poly (I:C) is manufactured from the individual homopolymers Poly Inosine (I) and Poly Cytidine (C). Poly I and Poly C are synthesized by individually polymerizing the nucleoside diphosphates inosine and cytidine in the presence of polynucleotide phosphorylase (PNPase). Each nucleoside diphosphate is individually polymerized by PNPase for a 20-24 hrs. to control the length of the resulting ribonucleic acid polymer. The enzyme, protein kinase, is then added to terminate the polymerization reaction. The resulting homopolymers (i.e. single stranded RNA molecules) are hydrolyzed to control the molecular weight range of each polymer product within a specified range. The hydrolyzed product is treated with ethanol to precipitate the single stranded RNA molecules (ssRNA) from solution. The precipitate is separated from the supernatant and dissolved in water. The solution of ssRNA is then filtered to remove particulates, ultra filtered to remove the low-molecular weight contaminants and then lyophilized. Lyophilized ssRNA products are individually tested for purity, molecular weight, and other quality attributes to ensure the products are within specification.

The individual single stranded homo-polymers (Poly I and Poly C) are individually dissolved in 0.015 M sodium chloride and then combined to anneal the strands forming the double stranded duplex product (Poly I:Poly C). After mixing, the resulting solution is filtered. The filtrate is ultra filtered to remove low molecular weight contaminants. The ultra filtered product is then lyophilized. The resulting duplex product is stored at −20° C. The lyophilized dsRNA product is tested for purity, molecular weight, and other quality attributes to ensure the product is within specification.

Example 1

In Vitro Biological Activity of Poly (I:C)

Materials & Methods
Polyinosinic-polycytidylic acid sodium salt (Poly (I:C). Midland Certified Reagent Company Inc (Texas, USA), lot 020905, partially pregelatinized maize starch, Stada AG (Bad Vilbel, Germany), lot 93301-9628, Sodium carboxymethylcellulose (Blanose 7MF), Ashland Aqualon (Wilmington, Del. USA) lot 3-30172, Dipalmitoylphosphatidylcholine (Lipoid PC 16:0/16:0), Lipoid GmbH (Ludwigshafen, Germany), lot 563098-01/049, Lactose monohydrate (#316 Fast Flo). Foremost (Banaboo, Wis., USA), lot 8509052261. Sodium alginate (Protanal LF10/60LS), FMC Biopolymer (Drammen, Norway), lot S19616, Absolute ethanol Chem-Lab (Zedelgem, Belgium), lot 17.2712904.400

In Vitro Biological Activity of Poly (I:C)
Poly (I:C) sensitive A549 cells (carcinomic human alveolar epithelial cells) were infected with a vector that contains the long IFN-β1 promoter (chromosome 9 from position 21069463 to 21067869), coupled to the Green Fluorescent Protein (GFP) and Renilla Luciferase construct (B1L-GAR5 construct). Upon stimulation with Poly (I:C), the IFN pathway is activated resulting in the activation of the B1L-GAR5 reporter construct and expression of the GFP and luciferase reporter genes. To obtain a highly responsive cell clone, Poly (I:C) stimulated cells were sorted for high GFP expression with a FACS Aria flowcytometer (Becton Dickinson) and out of >200 clones, the H10 clone was selected based on the % of Poly (I:C) responsive cells. A549-B1L-GAR5-H10 cells were grown until the tissue-culture flasks were confluent with cells after which the medium was refreshed and the cells were cultured for an additional four days. Then the cells were harvested using standard trypsinization, counted and were plated in 96 well flat bottom plates at 50.000 cells per well and stimulated overnight with Interferon β (75 U/ml) in 100 μl. The next day, 100 μl Poly (I:C)-carrier polymer mixtures were added to the cells at a ratio of Poly (I:C): polymer=1:5, resulting in 200 μl final volume, and the cells were incubated for an additional 24 h. After the incubation, the cells were harvested (by trypsin-mediated detachment) and analyzed on a BD-Calibur flowcytometer.

Example 2

Generation and Characterization of Poly (I:C) Micro Particles

Spray drying of Poly (I:C) with carrier polymers

The Alginate, CMC (Blanose) and partially pregelatinized maize starch spray dry process was performed on a B90 Nano spray dryer and on a Buchi B290 Mini spray dryer (Buchi, Flawil, Switzerland). In general, spray drying experiments with the B90 Nano spray dryer resulted in poor yields due to the high viscosity of the solutions. Demineralized water was filtered using a 0.2 micron cellulose acetate filter (Whatman FP30/0.2 CA-S) and added to a glass beaker The excipients were added while stirring using a magnetic stirrer. When completely dissolved, Poly (I:C) was added to the solution. A total solids concentration of 0.5% (w/w) and a ratio of Poly (I:C)/excipient 1/9 (w/w) was applied for all concepts. Compositions of the feed solutions are listed in Table 1A.

TABLE 1A

Feed compositions of Alginate, CMC and partially pregelatinized maize starch concepts

| material | Quantity (g) | | |
|---|---|---|---|
| | alginate | CMC | partially pregelatinized maize starch |
| Na-alginate (Protanal LF 10/60LS) | 1.35 | | |
| Na-CMC (Blanose 7 MF) | | 1.35 | |
| DDWM | | | 1.35 |
| Poly (I:C) | 0.15 | 0.15 | 0.15 |
| Demin water | 300 | 300 | 300 |

For the DPPC-Poly (I:C) concept, the solubility of DPPC (Dipalmitoylphosphatidylcholine) in different ethanol/water mixtures was determined. When spray drying pure DPPC, the yield obtained was low at about 25%. Therefore the addition of a carrier material was considered. Because of precipitation of Na-CMC, Na-alginate, waxy maize starch and malto-dextrin upon addition of ethanol, lactose was selected as a carrier for spray drying of Poly (I:C) with DPPC. Demineralized water was filtered using a 0.2 micron cellulose acetate filter (Whatman FP30/0.2 CA-S) and added to a glass beaker. Lactose was added while stirring using a magnetic stirrer. Once dissolved, both solutions were mixed and heated to 60° C. When completely dissolved, the solution was cooled to room temperature and poly I:C was added. A total solids concentration of 0.28% (w/w) and a ratio of Poly (I:C)/lactose/DPPC 1/2.25/6.75 (w/w/w) was applied. The composition of the feed solution is shown in Table 1B.

TABLE 1B

Feed compositions of DPPC concept

| material | Quantity (g) DPPC |
|---|---|
| DPPC (Lipoid PC 16:0/16:0) | 1.35 |
| Ethanol absolute | 430.80 |
| Lactose monohydrate (#316 Fast Flo) | 0.45 |
| Poly (I:C) | 0.20 |
| Demin water | 287.20 |

Spray drying of these solutions was performed in a lab scale spray dryer, type B 290 inert loop (Buchi, Flawil, Switzerland). The solutions were fed to a two-fluid nozzle (diameter: 0.7 mm) at the top of the spray dryer by means of a peristaltic pump, type 520U (Watson Marlow, Cornwall, UK). The spray dryer operated in co-current nitrogen flow mode. The spray dried particles were collected in a reservoir attached to a cyclone. After collection of the particles, the cyclone was cooled to room temperature. The collected powder was transferred to amber glass vials in a biohazard cabinet. The vials were flushed with nitrogen, closed and stored at 5° C. Process parameters are listed in Table 2.

TABLE 2

Process conditions

| Process parameter | Target value | | | |
|---|---|---|---|---|
| | alginate | CMC | partially pregelatinized maize starch | DPPC |
| Inlet drying nitrogen temperature (° C.) | 150 | 150 | 150 | 100 |
| Outlet drying nitrogen temperature (° C.) | 70 | 70 | 70 | 50 |
| Feed rate (g/min) | 4.0 | 4.1 | 4.0 | 5.3 |
| Condensor temperature (° C.) | NA | NA | NA | 10 |
| Drying nitrogen aspirator (%) | 100 | 100 | 100 | 100 |
| Atomizing nitrogen pressure drop (bar) | 0.3 | 0.3 | 0.3 | 0.3 |
| Oxygen concentration (%) | <6 | <6 | <6 | <6 |

Spray Drying of Additional Poly (I:C)-Partially Pregelatinized Maize Starch Concepts The spray dry process was performed on a Buchi B290 Mini spray dryer (Buchi, Flawil, Switzerland). Nuclease free water added to a glass beaker and the partially pregelatinzed maize starch is added while mixing using an Ultra Turax T25 (Janke & Kunkel), until the starch is completely dispersed. Poly (I:C) was dissolved in Nuclease free water and stirred on a magnetic stirrer until the Poly (I:C) is completely dissolved. The dissolved Poly (I:C) is added to the dispersed starch and stirred at room temperature, the Poly (I:C) solution is prepared just before spray drying. A total solids concentration of 10% (w/w) or 0.45% and a ratio of Poly (I:C)/Starch 1/200-1/100-1/50-1/24-1/9 (w/w) was applied. Feed compositions of these formulations are shown in table 3A.

TABLE 3A

Feed compositions partially pregelatinized maize starch concepts:

| material | Quantity (g) | | | | | |
|---|---|---|---|---|---|---|
| | 1/200 10% | 1/100 10% | 1/50 10% | 1/24 10% | 1/9 10% | 1/9 0.45% |
| Partially pregelatinized maize starch (g) | 50.25 | 25.25 | 25.5 | 12.5 | 9 | 4.5 |
| Poly (I:C) (g) | 0.25 | 0.25 | 0.500 | 0.500 | 1 | 0.5 |
| Nuclease free water (g) | 454.5 | 229.5 | 234 | 117 | 90 | 1106 |

The solutions were fed to a two-fluid nozzle (diameter: 0.7 mm) at the top of the spray dryer by means of a peristaltic pump. The spray dryer operated in co-current nitrogen flow mode. The spray dried particles were collected in a reservoir attached to a cyclone. After collection of the particles, the glass cylinder and cyclone was cooled to room temperature. The collected powder was transferred to amber glass bottle and this bottle is placed in an aluminum vapor lock bag. The vials were stored at room temperature. Process parameters are listed in Table 3B.

TABLE 3B

Process conditions

| Process parameter | 200/1-100/1-50/1-24/1-9/1 10% w/w | 9/1 0.45% w/w |
|---|---|---|
| Inlet drying nitrogen temperature (° C.) | 180 | 150 |
| Outlet drying nitrogen temperature (° C.) | 95-112 | 75-95 |
| Feed rate (g/min) | 6-9 | 5-6 |
| Condensor temperature (° C.) | 10 | 10 |
| Drying nitrogen aspirator (%) | 100 | 100 |
| Atomising nitrogen pressure drop (bar) | 0.3 | 0.4 |
| Oxygen concentration (%) | <6 | <6 |

Scanning Electron Microscopy

The samples were sputtered with gold particles with diameter +/−30-50 nm. Images were generated using a FEI scanning electron microscope-type Quanta 200F with Everhart Thornley detector.

Water Content-Karl Fischer Titration

Water content of the concepts was determined by means of a direct volumetric Karl Fisher titration. A KF TITRATOR V30 is used (Mettler Toledo, US). The powder (50-100 mg) was transferred to the titration vessel containing Hydranal® Methanol Dry (Sigma Aldrich) and stirred for 300 seconds. Titration was performed with Hydranal® Composite 2 (Sigma Aldrich) at a concentration of 2 mg/ml using a 5 ml burette. For termination a stop drift of 15 µg/min was applied. Samples were analyzed in triplicate.

Determination of Particle Size

There exists a tendency to evaluate particle size distribution data merely on the basis of the volume distribution of the products of interest. Thereby, one often limits the valuation to a comparison of the $D_v10$, $D_v50$ and $D_v90$ cumulative undersizes.

However, comparing $d_vx$ cumulative undersizes may not always be straight-forward due to the fact that different techniques and instruments readily lead to different results.

In addition, one can get more information out of a particle size (or shape) distribution data by looking from a different perspective to the data (i.e., using other parameters).

For the determination of the particle size distribution the laser diffraction test method was used.

The analysis was performed on a Malvern Mastersizer 2000 laser diffractometer equipped with a Hydro2000S wet dispersion module (or an equivalent system). The instrument is used in the blue light ON detection mode at a size range of 20 nm to 2 mm.

Example 3

In Vivo Testing of Formulations in the Influenza Mouse Model

All animal studies were approved by the ethical committee and performed according to national and international guidelines. 8-12 week old female Swiss mice (Janvier) were used. All intranasal treatments were performed under isoflurane anesthesia. To administer an amount of liquid, a droplet was applied directly on top of the nostril and, by closing the mouth, the droplet was allowed to enter via the nostril into the nasal cavity. Spray dried Poly (I:C)-carrier powders were freshly prepared just prior to each experiment and administrated in 15 µl liquid. Unformulated Poly (I:C) was administrated in phosphate buffered saline (PBS) at a concentration of 1 mg/ml. Pretreatment was typically performed on day 2 or 3 before challenge. The mice were challenged on day 0 with $10 \times LD_{90}$ mouse adapted H1N1 PR (FLU PR 1600517) in 25 µl (high volume challenge) or with $1 \times LD_{90}$ in 15 µl (low volume challenge). Following the challenge, mice were monitored daily for 14 days by measuring weight and behavior, mice were euthanized when weight loss was >20% compared to the day of challenge or when their behavior showed serious signs of illness.

Results

Selection of Carrier Polymers.

A requirement of a successful concept for the prevention of nasal common colds is that the biological activity of Poly (I:C) must be preserved in the final formulation. Therefore, a first step in the selection of carrier polymers for the spray-dry process was to identify polymers that do not inhibit the interferon stimulating capacity of Poly (I:C). Hereto, a number of carrier-polymers were mixed with Poly (I:C) in a 5:1 ratio (w:w) and added in titrated amounts to a Poly (I:C)-responsive interferon-promotor-GFP-reporter (A549-IFN-GAR5, clone H10) cell line (see materials and methods for details). The cells were incubated for 24 hours at 37° C. and 5% $CO_2$ after which the percentage of $GFP^+$ cells were measured on a flow cytometer. Increasing concentrations of Poly (I:C) result in a higher percentage of $GFP^+$ cells thus allowing us to use this in vitro model to assess the biological activity of Poly (I:C)-carrier mixtures (FIG. 1). Of the different carriers tested, Na-Alginate, partially pregelatinized maize starch, DPPC and blanose did not inhibit the Interferon stimulating capacity of Poly (I:C). In contrast, carbopol, K-carragenan, chitosan, and polyethylamine inhibited or completely blocked the interferon stimulating capacity of Poly (I:C). Based on these results, the carriers that do not affect Poly (I:C), Na-alginate (Protanal LF10/60LS, FMC Biopolymer), drum dried waxy maize starch (Cargill, via Stada), DPPC (Lipoid PC 16:0/16:0, Lipoid), and Na-CMC (Blanose 7MF) were selected for the next formulation development step.

Na-alginate is a gel-forming polysaccharide made up of mannuronic (M) and guluron (G) blocks. The strength and flexibility of the gel is defined by the G/M ratio. Na-CMC is a cellulose derivative with carboxymethyl groups. It is frequently used in nasal formulations, partially pregelatinized maize starch is an amylopectin based starch which is non-irritating to the mucosal tissue. The three excipients Na-alginate, Na-CMC and partially pregelatinized maize starch display good bioadhesive properties. DPPC is a phospholipid and the major constituent of pulmonary surfactant. It may enhance nasal absorption.

FIG. 1: Biological (Interferon) Stimulating Capacity of Poly (I:C) and Poly (I:C)-Carrier Mixtures.

Poly (I:C) responsive cells with a GFP-reporter construct expressed under the interferon-β-promotor were incubated with Poly (I:C)-carrier mixtures (in a 1:5 ratio) for 24 hours and subsequently analyzed for GFP-expression. Numbers on the Y-axis indicate the percentage of GFP+ cells of the total living cells in the sample. Numbers on the x-axis indicate the concentration of Poly (I:C) in the mixture. Representative results of two experiments are shown.

Spray-Dry Process and Biological Activity and Stability of the Concepts

The spray dry process was performed on a B90 Nano spray dryer and on a Buchi B290 Mini spray dryer (Buchi, Flawil, Switzerland). In general, spray drying experiments with the B90 Nano spray dryer resulted in poor yields due to the high viscosity of the solutions.

After each process the yield was calculated as the amount of powder collected in the reservoir divided by the theoretical amount of powder weighed for preparation of the feed. Results are listed in Table 4. The lower yield for Concept 4 can be explained by the observation of powder build-up in the cyclone, potentially caused by stickiness of DPPC at the local temperature in the cyclone during spray drying.

TABLE 4

Yield, weight of powder collected versus theoretical weight

| | Concept | | | |
|---|---|---|---|---|
| | Alginate (1) | CMC (2) | partially pregelatinized maize starch (3) | DPPC (4) |
| Process yield % w/w) | 77.7 | 74.1 | 86.2 | 52.0 |

Scanning Electron Microscopy

Figure 2:
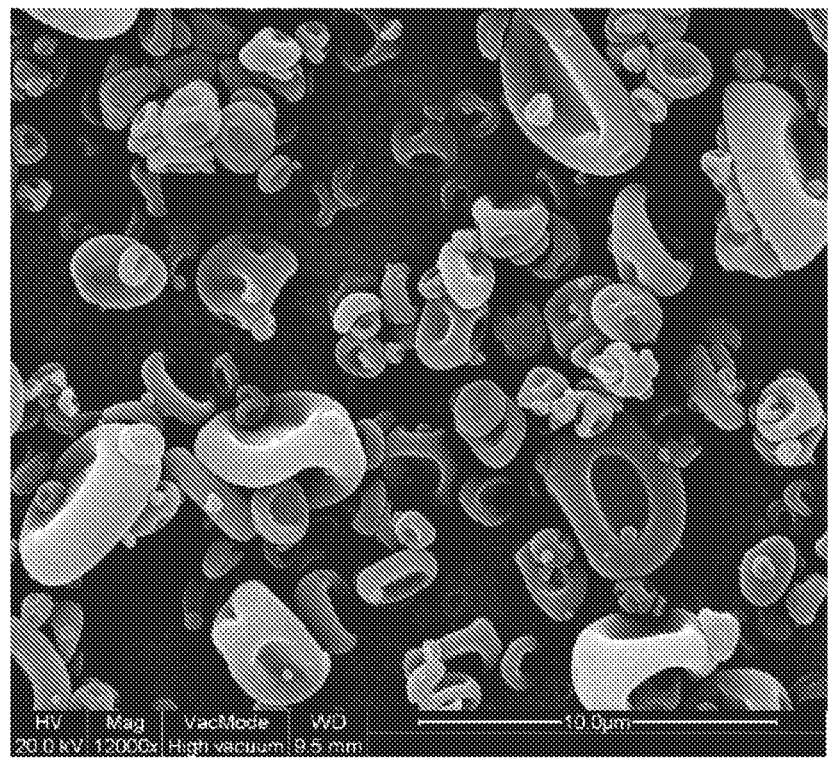
FIG. 2 shows scanning Electron microscopic picture of spray-dried partially pregelatinized maize starch-Poly (I:C) microparticles.
Figure 3A:
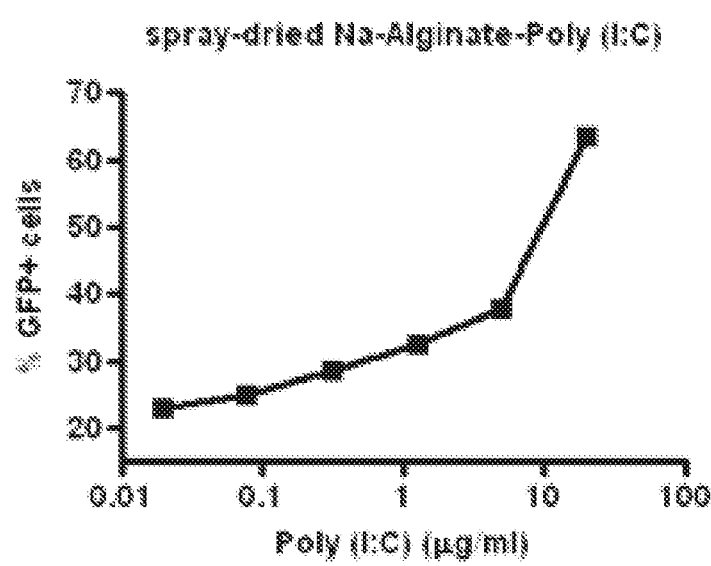
FIG. 3A shows biological (interferon) stimulating capacity of Poly (I:C)-Na-alginate carrier spray-dried concepts after one month storage at room temperature as assessed by GFP expression under the interferon-β-promoter. Poly (I:C) responsive cells with a GFP-reporter construct were incubated with Poly (I:C)-carrier mixtures for 24 hours and subsequently analyzed for GFP-expression. Numbers on the Y-axis indicate the percentage of GFP+ cells of the total living cells in the sample. Numbers on the x-axis indicate the concentration of Poly (I:C) in the mixture. Representative results of two experiments are shown.
Figure 3B:
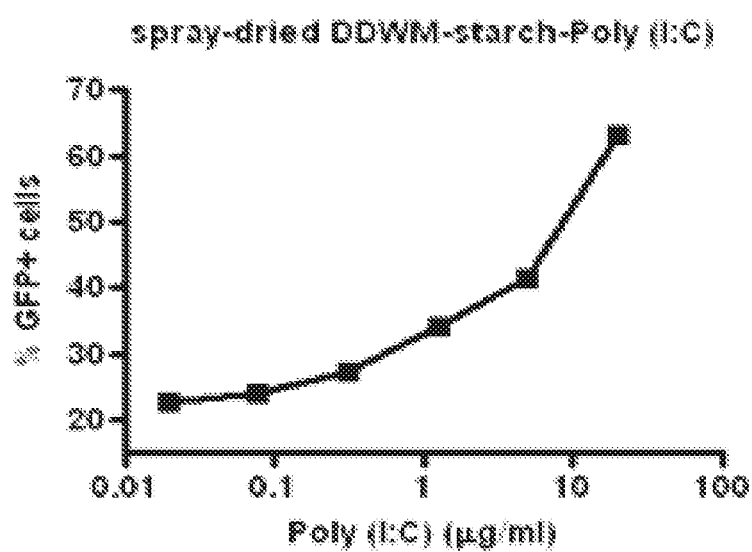
FIG. 3B shows the same experiment as described in FIG. 3A except that the carrier is DDWM-starch.
Figure 3C:
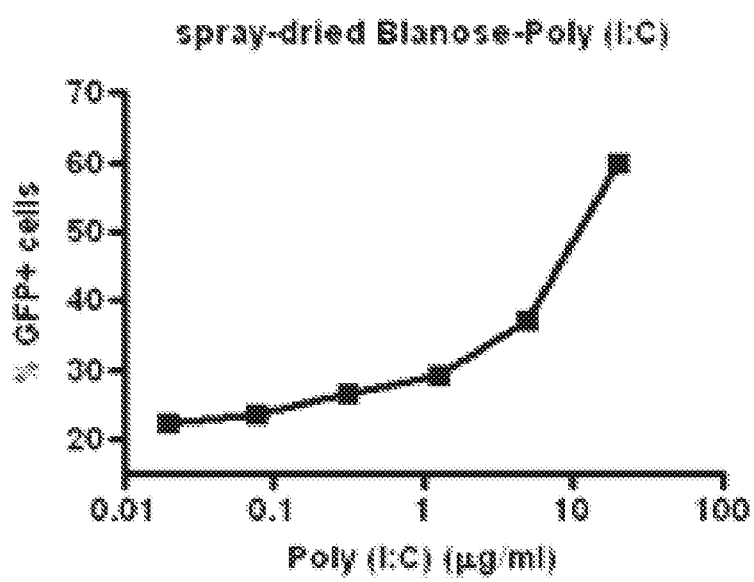
FIG. 3C shows the same experiment as described in FIG. 3A except that the carrier is blanose.
Figure 3D:
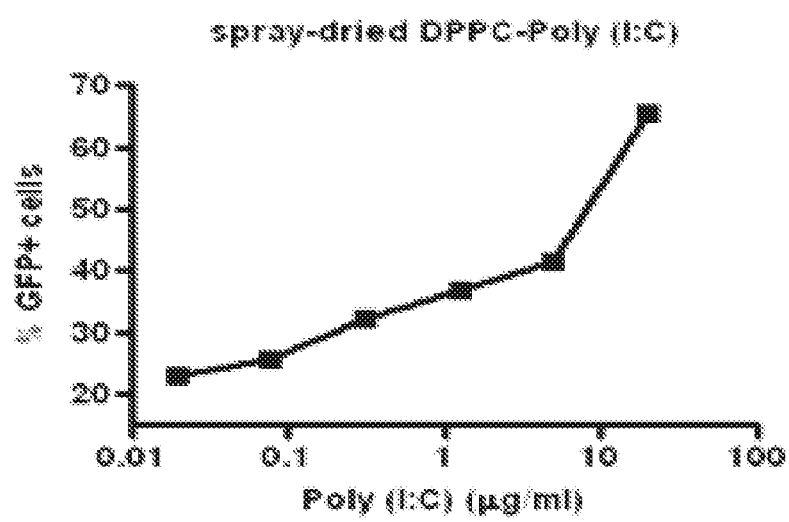
FIG. 3D shows the same experiment as described in FIG. 3A except that the carrier is DPPC.
Figure 3E:
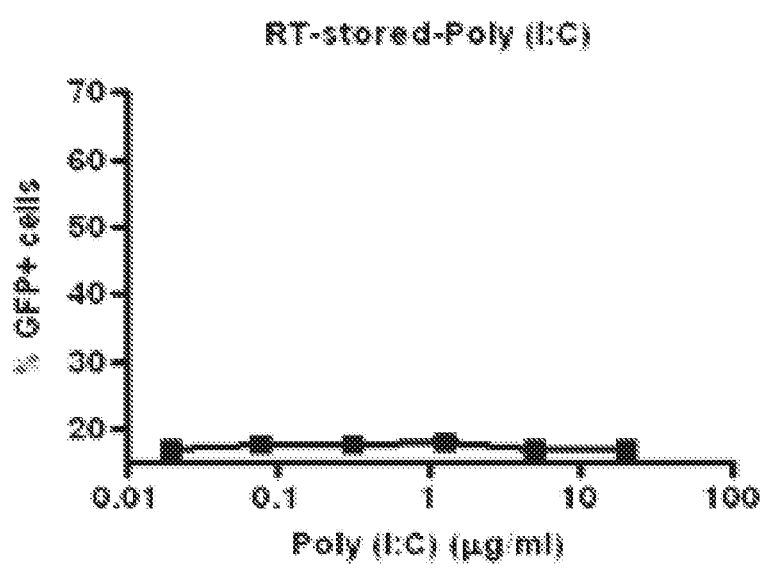
FIG. 3E shows the same experiment as described in FIG. 3A when the carrier is not present and poly(I:C) is stored at room temperature.
Figure 3F:
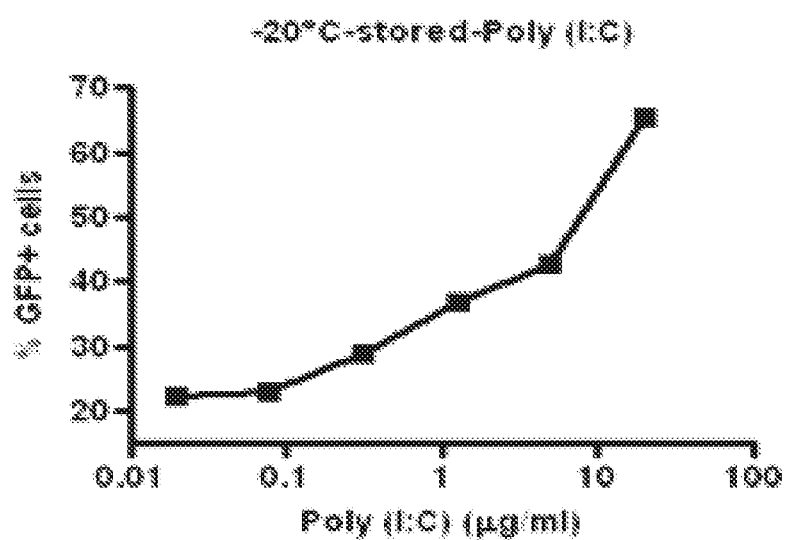
FIG. 3F shows the same experiment as described in FIG. 3A when the carrier is not present and poly(I:C) is stored at −20° C.

SEM images of the spray dried powder are shown in FIG. 2.

The powder of Concept 3 (partially pregelatinized maize starch) consisted of collapsed spheres. Laser diffraction measurements on the corresponding placebo powder resulted in a particle size with a $D_v50$ of 4.5 micrometer.

FIG. 2: Scanning Electron microscopic picture of spray-dried partially pregelatinized maize starch-Poly (I:C) microparticles.

Water Content.

The water content of the spray dried powder was determined. Residual water originates from water uptake from the environment and water used for spray drying process.

TABLE 5

Water content of the concepts after spray drying

| | Concept | | | |
|---|---|---|---|---|
| | Alginate (1) | CMC (2) | partially pregelatinized maize starch (3) | DPPC (4) |
| Water content (% w/w) | 8.2 | 7.48 | 7.38 | 3.61 |

Partially pregelatinized maize starch, NaCMC and Na-alginate are hygroscopic excipients, a characteristic required for bioadhesion through swelling and gel formation. This is reflected in the results listed in Table 5. For Concept 4, water content proved lower than those of concepts 1-3, most probably because the powder form Concept 4 was spray dried from an ethanol/water mixture. In addition, lactose is not hygroscopic and water uptake is restricted due to the lipophilic nature of DPPC in this concept.

Stability of Poly (I:C)-Concepts at Room Temperature

One important characteristic for an anti-common cold formulation is that the concept should be stable at room temperature (RT) in order to facilitate storage and guarantee activity of the active component of the product. However, Poly (I:C) is very unstable when dissolved in water containing solvents as it is degraded by hydrolysis or by RNase enzymes. Especially RNase enzymes are known to be ubiquitously present and RNase contamination would result in a rapid breakdown of the Poly (I:C) RNA molecules.

To test the stability, the four concepts were stored at room temperature. Poly (I:C) in PBS stored at RT or at −20° C. were used as controls. After one month of storage, the biological activity of the concepts and controls was assessed by measuring the interferon-reporter response of the concepts on a Poly (I:C) responsive cell line. All spray-dried Poly (I:C) concepts showed unaltered activity vs the −20° C. stored Poly (I:C) on the Poly (I:C) sensitive cell line (FIG. 3). In contrast RT stored Poly (I:C) in PBS completely lost its interferon-stimulatory activity. These results show that the spray dried formulations are very stable when stored at room temperature in contrast to Poly (I:C) in water containing liquids.

FIG. 3: Stability of Poly (I:C) Concepts after One Month Storage at Room Temperature.

Poly (I:C) responsive cells with a GFP-reporter construct were incubated with Poly (I:C)-carrier mixtures for 24 hours and subsequently analyzed for GFP-expression. Numbers on the Y-axis indicate the percentage of GFP+ cells of the total living cells in the sample. Numbers on the x-axis indicate the concentration of Poly (I:C) in the mixture. Representative results of two experiments are shown.

In Vivo Prophylaxis Using a Mouse Influenza Challenge Model

Poly (I:C) is known in literature for its anti-viral effects. However, in order to show in vivo efficacy in a mouse influenza model, it had to be given on consecutive days or in water/liposome formulations. Back in 1972 it had been shown that Poly (I:C) was effective as an anti-viral prophylaxis treatment in a human trial in which volunteers were challenged with human Rhino virus (HRV) or with influenza virus. In this study however, Poly (I:C) had to be given every two hours. As our spray dried concepts showed similar in vitro biologic activity and increased RT stability compared to Poly (I:C) in PBS, we engaged into in vivo testing in order to test the anti-viral activity of the different concepts. To this end, mice were treated with a single intranasal dose of (spray-dried) Poly (I:C) formulation several days before the high volume (25 µl) influenza challenge on day 0. The spray-dried concepts were applied using a small volume (15 µl) of organic carrier solvents (ethanol or ethanol/glycerol 1/1 w/w) in order to prevent dissociation of the particles. Weight loss (relative to day 0), general behavior and survival were monitored for 14 days (see material and methods for more details). Interestingly, we observed that a single treatment with Poly (I:C) in PBS as well as spray-dried partially pregelatinized maize starch-Poly (I:C) in PBS only had a very minor prophylactic effect on the influenza challenge as indicated by non-significant protection of the mice in terms of weight loss and survival (Table 6). One explanation for this is that the spray-dried partially pregelatinized maize starch (I:C) dissolved in PBS and therefore gave a similar response as Poly (I:C). Poly (I:C) in PBS was slightly more effective when given on two consecutive days, although the difference with placebo control mice was not significant. Surprisingly, the partially pregelatinized maize starch-Poly (I: C) concept in ethanol required just a single treatment in order to confer significant protection against the influenza challenge, resulting in superior survival. Apparently the microsphere particle form of partially pregelatinized maize starch-Poly (I:C) is a crucial part of the mechanism of action that results in the superior protection against influenza.

TABLE 6

Survival of (formulated) Poly (I:C) treated influenza challenged mice.

| Treatment groups* | solvent | details | | |
|---|---|---|---|---|
| | | Total Poly (I:C) per mouse (µg) | % surviving mice | P value vs placebo |
| placebo | PBS | 0 | 0 | — |
| Poly (I:C) day −2 | PBS | 40 | 0 | N.S. |
| Poly (I:C) day −2, −1 | PBS | 80 | 20 | N.S. |
| partially pregelatinized maize starch-Poly (I:C) | PBS | 40 | 0 | N.S. |
| partially pregelatinized maize starch-Poly (I:C) | ethanol | 40 | 60 | 0.04 |

*= 5 mice per group, representative results of two experiments are shown, P value calculated using Kaplan-Meier log rank statistics.
N.S. = not significant In a next experiment, we compared if ethanol as a carrier solvent had any effect on the severity of the influenza challenge. In Table 7, the results are shown of ethanol vs PBS placebo treated mice. In this experiment the influenza challenge was a bit less aggressive as compared to the challenge used in the Table 6 experiment, which allowed us to observe a positive or negative effect of the ethanol pretreatment on the survival after influenza challenge. We observed that ethanol treated mice experienced a very similar sensitivity to the influenza challenge as compared to PBS pretreated mice. We conclude therefore that ethanol is not actively contributing to the anti-viral effect and can therefore be used as intranasal administration carrier solvent that preserves the microsphere particle form of the concepts. Of note, unformulated Poly (I:C) could not be applied in ethanol as Poly (I:C) precipitated in ethanol thus preventing a controlled application of Poly (I:C)

TABLE 7

Survival of ethanol- and PBS-placebo treated mice after influenza challenge

| Treatment groups* | solvent | details | | |
|---|---|---|---|---|
| | | Total Poly (I:C) per mouse (µg) | % surviving mice | P value vs placebo |
| placebo | PBS | 0 | 33 | — |
| Ethanol placebo | ethanol | 0 | 33 | N.S. |

*= 6 mice per group, P value calculated using Kaplan-Meier log rank statistics.
N.S. = not significant In the next step, we addressed the question if spray-drying of the concept to generate particles of partially pregelatinized maize starch-Poly (I:C) or just mixing of ingredients is required/sufficient to observe the anti-viral effects. Hereto, we mixed dry powder Poly (I:C) with dry powder starch (mixed Poly (I:C)-starch) and compared this with spray-dried starch-Poly (I:C) and placebo. We observed (Table 8) that mixed partially pregelatinized maize starch-Poly (I:C) had no significant protective effect on the influenza challenge, in contrast to the spray-dried formulation of partially pregelatinized maize starch-Poly (I:C), which again resulted in a superior and significant protection against the influenza challenge.

TABLE 8

Survival of mixed versus spray dried partially pregelatinized maize starch-Poly (I:C) treated mice after influenza challenge

| Treatment groups* | solvent | details | | |
|---|---|---|---|---|
| | | Total Poly (I:C) per mouse (µg) | % surviving mice | P value vs placebo |
| placebo | PBS | 0 | 0 | — |
| Mixed partially pregelatinized maize starch-Poly (I:C)** | ethanol | 10 | 25 | N.S. |
| Spray-dried partially pregelatinized maize starch-Poly (I:C) | ethanol | 10 | 60 | 0.03 |

*= 6 mice per group,
**= 4 mice, P value calculated using Kaplan-Meier log rank statistics.
N.S. = not significant In order to test if the spray-dried micro particles could also be administrated in an other organic solvent we tested the use of Glycerol as carrier solvent for the Poly (I:C) micro particles. The use of this carrier was also possible and resulted in significant protection, however the high viscosity of glycerol proved to make it rather difficult to apply a nose drop intranasal. We therefore tested a 1/1 mixture of ethanol/glycerol to apply the micro particles. In Table 9 the results of this experiment are shown and clearly indicate that a single administration of the micro particles in ethanol/glycerol results in a significant improved survival from the influenza challenge as compared to placebo (ethanol/glycerol alone).

TABLE 9

Survival spray dried Partially pregelatinized maize starch-Poly (I:C) treated mice using ethanol/glycerol as carrier solvent

| | | details | | |
|---|---|---|---|---|
| Treatment groups* | solvent | Total Poly (I:C) per mouse (μg) | % surviving mice | P value vs placebo |
| placebo | Ethanol/glycerol | 0 | 0 | — |
| Spray-dried partially pregelatinized maize starch-Poly (I:C) | Ethanol/glycerol | 10 | 78 | <0.01 |

*= 9 mice per group, P value calculated using Kaplan-Meier log rank statistics.

In a next step we tested the use of a different carrier polymer in the spray-dried formulation of Poly (I:C). Hereto we compared placebo treated mice, with Poly (I:C) treated mice and with either spray dried partially pregelatinized maize starch-Poly (I:C) or spray dried Na-alginate-Poly (I:C). We observed that only spray-dried micro particles of Poly (I:C) protected mice from severe weight loss caused by a subsequent challenge with influenza (see Table 10). Poly (I:C) alone did not protect against weight loss. These results indicate that the combination of Poly (I:C) with a carrier polymer in a spray-dried micro particle is required to confer sufficient protection against a viral pathogen. The nature of the carrier polymer is of less importance as long as the micro particle structure is preserved (see table 6, spray-dried-partially pregelatinized maize starch-Poly (I:C) is not effective when dissolved in PBS).

TABLE 10

Weight loss of spray dried partially pregelatinized maize starch-Poly (I:C) and Na-Alginate-Poly (I:C) treated mice

| | | details | | |
|---|---|---|---|---|
| Treatment groups* | solvent | Total Poly (I:C) per mouse (μg) | % weight retained at day 4 | P value vs placebo |
| placebo | Ethanol/glycerol | 0 | 85.99 | — |
| Poly (I:C) | PBS | 10 | 87.04 | N.S. |
| Spray-dried partially pregelatinized maize starch-Poly (I:C) | Ethanol/glycerol | 10 | 92.82 | 0.006 |
| Spray-dried Na-Alginate-Poly (I:C) | Ethanol/glycerol | 10 | 90.91 | 0.007 |

*= 12 mice per group, P value calculated using unpaired two-tailed T-test statistics.
N.S. = not significant Finally, we compared different partially pregelatinized maize starch-Poly (I:C) formulations with each other and with unformulated Poly (I:C) in PBS in order to identify the concentration of Poly (I:C) that is required in the formulation, as well as the micro particle size that is required in the formulation. Hereto, we produced additional spray dried partially pregelatinized maize starch/Poly (I:C) in the ratio's 50/1 and 100/1 and 200/1, as well as partially pregelatinized maize starch/Poly (I:C) with a particle size of $(D_v 50)$ 9 μm (1/9, 0.45%) and $(D_v 50)$ 17 μm (1/9, 10%) respectively. The results of the comparison of these formulations with unformulated Poly (I:C) are shown in Table 11. We observed that a concentration of Poly (I:C) between 1/100 to 1/9 results in a good protection against influenza. Diluting the Poly (I:C) more in starch resulted in less efficient and non-significant protection. In addition, we observed no major difference in the two batches with different particle size, indicating that a particle size $(D_v 50)$ between 9 μm and 18 μm is sufficient to confer effective protection by the Poly (I:C) micro particles.

TABLE 11

Weight loss of influenza challenged mice treated with additional concepts of spray dried partially pregelatinized maize starch-Poly (I:C)

| | | details | | |
|---|---|---|---|---|
| Treatment groups* | solvent | Total Poly (I:C) per mouse (μg) | % weight retained at day 4 | P value vs Poly (I:C) (PBS) |
| Poly (I:C) | PBS | 10 | 82.9 | — |
| Spray-dried partially pregelatinized maize starch/Poly (I:C) (50/1) | Ethanol/glycerol | 10 | 103.5 | <0.02 |
| Spray-dried partially pregelatinized maize starch/Poly (I:C) (100/1) | Ethanol/glycerol | 10 | 97.2 | <0.02 |
| Spray-dried partially pregelatinized maize starch/Poly (I:C) (200/1) | Ethanol/glycerol | 10 | 90.71 | NS |
| Spray-dried partially pregelatinized maize starch/Poly (I:C) (9/1, 0.45%) | Ethanol/glycerol | 10 | 99.62 | <0.02 |
| Spray-dried partially pregelatinized maize starch/Poly (I:C) (9/1, 10%) | Ethanol/glycerol | 10 | 99.56 | <0.02 |

*= 8 mice per group, P value calculated using unpaired two-tailed T-test statistics.
N.S. = not significant

CONCLUSION 4 powder concepts have been produced by spray drying for nasal delivery of Poly (I:C). Concepts with Na-alginate (Concept 1), Na-CMC (Concept 2), partially pregelatinized maize starch (Concept 3) and DPPC (Concept 4) were selected based on a bioactivity screen and on process ability. All four concepts were tested in vitro to determine the biological activity and stability of Poly (I:C) in the formulation. Our results indicate that the spray dry process has no negative effect on the bioactivity of Poly (I:C). In addition, the formulations are stable at room temperature, in contrast to Poly (I:C) dissolved in PBS.

In a next step we tested the concepts 1 and 3 in the prophylaxis of influenza using a murine influenza challenge model. Based on literature, experiments were started with the intention that concepts 1 and 3 should have a similar protective effect as unformulated Poly (I:C) (in PBS). Surprisingly, it was found that concepts 1 and 3 were superior to Poly (I:C) in protecting mice against a subsequent challenge with influenza. It appeared that a single dose of unformulated Poly (I:C) is not very efficient in protecting mice, but that Poly (I:C) needed to be administrated several times in order to be more effective. However a single administration of formulated Poly (I:C) (concepts 1 and 3) protected mice significantly. Furthermore, it was shown that the micro particle structure is crucial (as PBS dissolved micro particles lost activity in vivo (table 6) but not in vitro (FIGS. 1 and 2)). To preserve particle size, we administrated the micro particles in ethanol or in ethanol/glycerol carrier solvents. Particle size ($D_v50$) between 9 micrometer and 17 micrometer were effective. Poly (I:C) was effective at dilutions 100/1 to 9/1 (starch/Poly (I:C)).

In conclusion, we have identified new concepts that improves the in vivo efficacy of a single dose intranasal Poly (I:C) administration in order to confer prophylactic protection against a subsequent lethal challenge of influenza.

The invention claimed is:

1. A method for protecting against a human influenza virus infection or a human rhinovirus infection, comprising nasally administering to a human in need thereof a prophylactically effective amount of a composition, wherein:
    the composition consists of microparticles; and
    the microparticles consist of polyinosinic acid, polycytidylic acid, water, and carrier polymer, wherein the carrier polymer is starch, blanose, alginate or dipalmitoylphosphatidylcholine (DPPC).

2. The method of claim 1, wherein the carrier polymer is a pregelatinized starch or a partially pregelatinized starch.

3. The method of claim 1, wherein the carrier polymer is alginate, blanose, or dipalmitoylphosphatidylcholine (DPPC).

4. The method of claim 1, wherein the ratio of polyinosinic acid and polycytidylic acid to the carrier polymer in the microparticles is between 1:100 (w/w) and 1:1 (w/w).

5. The method of claim 4, wherein the ratio of polyinosinic acid and polycytidylic acid to the carrier polymer in the microparticles is between 1:12 (w/w) and 1:9 (w/w).

6. The method of claim 5, wherein the carrier polymer is starch.

7. The method of claim 1, wherein the average chain length of the polyinosinic acid and polycytidylic acid is approximately 300 base pairs to 6,000 base pairs.

8. The method of claim 1, wherein the average molecular weight of the polyinosinic acid and polycytidylic acid is approximately 180 kDa to 3,600 kDa.

9. The method of claim 1, wherein the microparticles of the composition have an average particle size between 0.1 μm and 100 μm.

10. The method of claim 1, wherein the microparticles of the composition have a $D_v50$ from 0.1 μm to 200 μm.

11. The method of claim 10, wherein the microparticles of the composition have a $D_v50$ from 10 μm to 20 μm.

12. The method of claim 1, wherein the composition is a dry powder.

13. The method of claim 1, wherein the microparticles are produced by a spray-dry process.

14. A method for protecting against an influenza virus infection, comprising administering to a human patient in need thereof a therapeutically effective amount of a composition, wherein:
    the composition is a dry powder;
    administering the composition comprises nasal administration;
    the composition consists of microparticles;
    the microparticles consist of polyinosinic acid, polycytidylic acid, and water mixed with a starch; and
    the microparticles have an average particle size between 0.1 μm and 100 μm.

15. A method for protecting against a human rhinovirus infection, comprising administering to a human patient in need thereof a therapeutically effective amount of a composition, wherein:
    the composition is a dry powder;
    administering the composition comprises nasal administration;
    the composition consists of microparticles;
    the microparticles consist of polyinosinic acid, polycytidylic acid, and water mixed with a starch; and
    the microparticles have an average particle size between 0.1 μm and 100 μm.

16. The method of claim 1, wherein the carrier polymer is starch.

17. The method of claim 1, wherein the microparticles consist of polyinosinic acid and polycytidylic acid mixed with carrier polymer, wherein the carrier polymer is starch, blanose, alginate or dipalmitoylphosphatidylcholine (DPPC).

* * * * *